United States Patent
Laghi

(10) Patent No.: US 6,676,708 B1
(45) Date of Patent: Jan. 13, 2004

(54) PROSTHETIC FOOT WITH DIFFERENTIATED HEEL ELASTICITY AND SPLIT UPPER ANKLE

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

(21) Appl. No.: 10/064,844

(22) Filed: Aug. 22, 2002

(51) Int. Cl.$^7$ .................................................. A61F 2/66
(52) U.S. Cl. .......................................... 623/52; 623/55
(58) Field of Search ............................. 623/52, 53, 55, 623/56

(56) References Cited

U.S. PATENT DOCUMENTS 5,653,767 A * 8/1997 Allen et al. .................... 623/52
5,944,760 A * 8/1999 Christensen ................. 623/55

FOREIGN PATENT DOCUMENTS

DE  298 20 904 U1 * 4/1999 ............. A61F/2/00

* cited by examiner

Primary Examiner—David H. Willse
(74) Attorney, Agent, or Firm—Ronald E. Smith; Smith & Hopen , PA

(57) ABSTRACT

A dynamic prosthetic foot has a split upper ankle and exhibits differentiated heel elasticity. The ankle diverges upwardly from a sole along a transverse parting line and includes a horizontal and a vertical part. The horizontal part is supported by a horizontal leading end of a central support that forms one of four parts that collectively form the heel of the prosthetic foot. A downwardly turned return bend is formed in the trailing end of the central support and a central extension extends in trailing relation to a free end of the central support. A lateral heel extension and a medial heel extension are formed integrally with the sole and flank the central extension. Each of the four heel parts absorb impacts generated during ambulation and therefore provide differentiated heel elasticity.

13 Claims, 4 Drawing Sheets

PROSTHETIC FOOT WITH DIFFERENTIATED HEEL ELASTICITY AND SPLIT UPPER ANKLE

BACKGROUND OF INVENTION

1. Field of the Invention

This invention relates, generally, to the art of prosthetics. More particularly, it relates to improvements in prosthetic feet.

2. Description of the Prior Art

During normal ambulation, the first part of a foot to contact the ground is the trailing end of the heel. This initial contact between heel and ground is known as the "heel strike." The trailing end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet are quite rigid and provide little or no cushion to the impact on the ground at the moment of "heel strike" and little or no elastic response at "push off." The shock of impact is thus transmitted directly to the skeletal structure of the user, and the lack of elastic response forces an unnatural gait.

Perhaps the earliest prosthetic foot that provides an elastic response at heel strike and push off is disclosed in U.S. Pat. No. 4,547,913 to Phillips, assigned to Flex Foot, Inc. Multiple versions of that device have been developed. The original version is formed of a carbon fiber epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a vis the pre-1980's prosthetic feet, the reduced impact is transmitted vertically to the skeletal structure of the user, and the elastic response in a vertical plane causes a four to six millimeter bounce at heel strike. This vertical response causes an unnatural walk because a healthy human heel is soft at the trailing end where heel strike occurs and is hard on the bottom so that it can support the entire weight of the body. Thus, the normal gait of a human includes a rolling motion as the trailing end of the heel strikes the ground; there is no vertical motion causing the heel to bounce upon ground impact.

Accordingly, there is a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet of the type heretofore known, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less rigid inner or medial edge. In this way, the prosthetic foot takes advantage of the presence of the natural foot, i.e. , the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for an improved dynamic prosthetic foot is now met by a new, useful, and nonobvious dynamic prosthetic foot having a split upper ankle and a heel with differentiated elasticity. The novel prosthetic foot includes a sole and an ankle part that separates from the sole along a transverse parting line. The transverse parting line is approximately half way between a toe end of the sole and a heel end of the prosthetic foot.

The ankle part includes a gradual upward bend, a horizontal part, and a vertically extending part that provides a pair of transversely spaced apart pylon supports.

The novel prosthetic foot further includes a heel part formed integrally and generally coplanar with the sole.

The heel part includes a central support, a central extension, a lateral heel extension, and a medial heel extension.

The central support has a leading end disposed in underlying, supporting relation to the horizontal part of the ankle part and a downwardly turned return bend formed in a trailing end thereof.

The central extension has a leading end secured to a trailing free end of the central support and a trailing end having a gradual upward bend formed therein.

The lateral heel extension and the medial heel extension are disposed on opposite sides of the central support and the central extension.

Accordingly, the central support, central extension, lateral extension, and medial extension of the heel part provide differentiated responses to impact forces created by ambulation.

A vertically extending slot is formed in the vertically extending part of the ankle part, mid-breadth thereof to divide said vertically extending part into two equal size parts. The two equal size parts form the lateral pylon support and the medial pylon support. The lateral pylon support is adapted for connection to a first prosthetic pylon and the medial pylon support is adapted for connection to a second prosthetic pylon. More particularly, a lateral pylon connector adapted to receive the lateral pylon is secured to the lateral pylon support along a trailing, heel side thereof and a medial pylon connector adapted to receive the medial pylon is secured to the medial pylon support along a trailing, heel side thereof.

The central extension has a trailing end that trails the respective trailing ends of the lateral heel extension and the medial heel extension. The leading end of the central extension is coextensive with the free end of the central support.

In a second embodiment of the invention, elongate lateral and medial pylons supplant the lateral and medial pylon supports and the lateral and medial pylon connectors secured thereto. The lateral and medial pylons are about twenty inches in length and are cut to size as needed by a prosthetist at the time of fitting the novel foot to a patient. The uppermost ends of the lateral and medial pylons are connected to the prosthetic socket that receives the residual limb.

An important object of this invention is to provide a prosthetic foot having heel elasticity in a direction parallel to the ground.

Another important object is to provide a prosthetic foot having a smooth transition from heel strike to push off.

Yet another object is to provide a prosthetic foot having differentiated medial and lateral stiffness so that an instability tends to shift weight from the lateral edge of the prosthetic foot to the medial edge thereof, just as in a natural foot.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
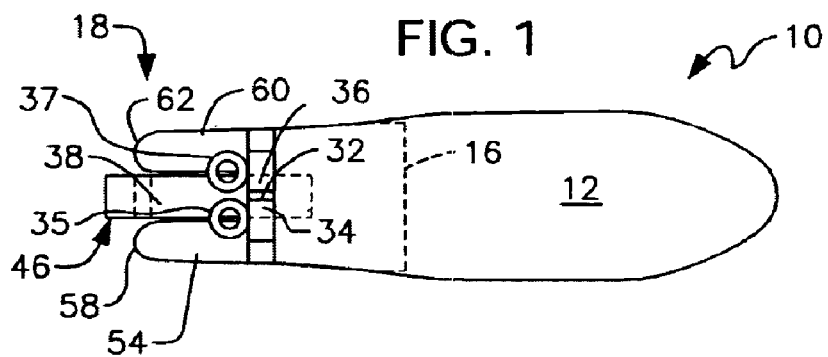
FIG. 1 is a top plan view of a first embodiment of a prosthetic foot with differentiated heel elasticity.
Figure 2:
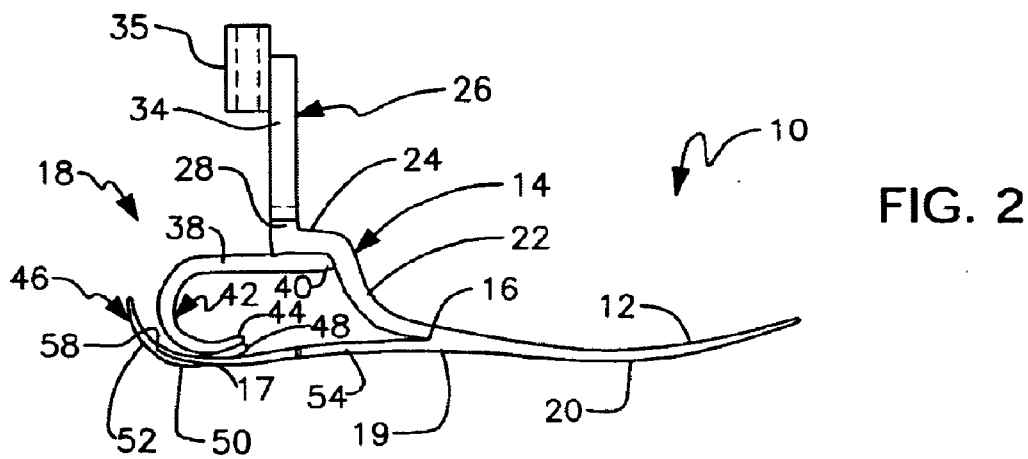
FIG. 2 is a side elevational view thereof.
Figure 3:
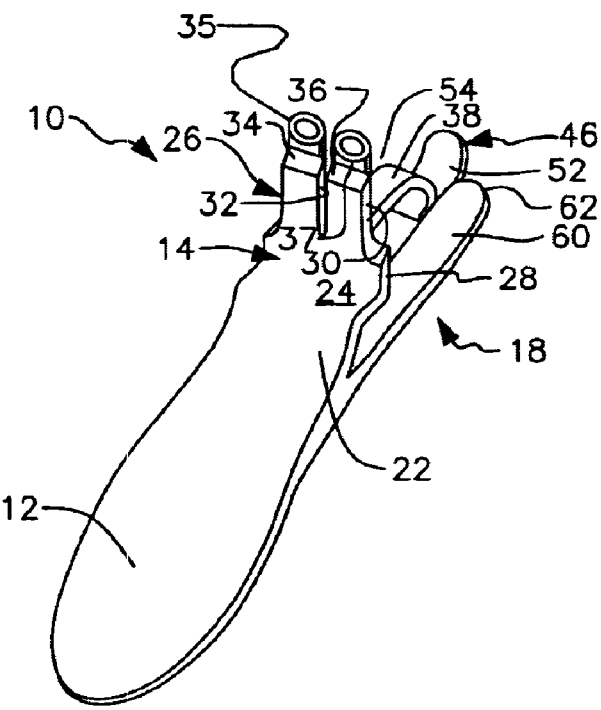
FIG. 3 is a perspective view thereof.

Referring to FIGS. 1–3, it will there be seen that the reference numeral 10 denotes an illustrative embodiment of the novel dynamic prosthetic foot with differentiated heel elasticity. In this first embodiment, a split upper ankle is provided.

Prosthetic foot 10 includes a sole 12, an ankle part 14 that separates from sole 12 at transverse parting line 16, and a heel 18.

First convexity 17 is formed in each of the lateral and medial heel extensions 54, 60 and provides the function of the bottom of a natural heel. Concavity 19 is formed in sole 12, mid-length thereof, and performs the function of a natural arch. Second convexity 20 is longitudinally spaced from concavity 19 and performs a function corresponding to the function performed by the ball of a natural foot.

Ankle part 14 includes a first upwardly-turned (with respect to sole 12) gradual bend 22, horizontal part 24, and vertical part 26. As perhaps best understood in connection with FIG. 3, vertical part 26 includes a lower part 28 having a breadth equal to that of horizontal part 24 and an upper part 30 of reduced breadth.

Reduced breadth upper part 30 has a vertically-extending slot 32 formed midbreadth thereof that divides said upper part 26 into lateral upper part 34 and medial upper part 36. Parts 34, 36 share a common height, breadth, and thickness or longitudinal extent and are transversely spaced apart from one another as depicted. Said parts form lateral pylon connector 34 and medial pylon connector 36.

Lateral pylon connector 35 is secured to the trailing, heel side of lateral pylon connector 34 and medial pylon connector 37 is secured to the trailing, heel side of medial pylon connector 36.

A first elongate prosthetic pylon, not shown, is received within pylon connector 35 and a second elongate prosthetic pylon, not shown, is connected to medial pylon connector 37.

Heel 18 has four parts. The first part of heel 18 is central support 38, the second part is central extension 46, the third part is lateral heel extension 54, and the fourth part is medial heel extension 60.

Central support 38 has a leading part 40 that underlies and supports horizontal part 24 of ankle part 14. A downwardly turned return bend 42 is formed in the trailing end of central support 38 and said return bend terminates in a free leading end 44 that is angled upwardly slightly, relative to a horizontal plane, as depicted in FIG. 2.

Central extension 46 has a leading end 48 secured by suitable means to said free, leading end 44 of return bend 42. A convexity 50 is formed in central extension 46 and said central extension terminates in a gradually upwardly turned trailing bend 52. Significantly, trailing bend 52 is positioned at the trailing end of prosthetic foot 10 and is therefore the first part of said foot 10 to contact the ground during ambulation.

Convexities 17 and 50 are closely spaced relative to one another and collectively perform the function of the bottom of a natural heel.

Lateral heel extension 54 separates from sole 12 at transverse parting line 16. Convexity 17 is formed therein near its trailing end 58.

Medial heel extension 60 has a construction like that of lateral heel extension 54, and terminates in trailing end 62 (FIGS. 1 and 3).

Free trailing ends 58, 62 of lateral heel extension 54 and medial heel extension 60, respectively, are positioned in leading relation to the trailing end of central extension 46. Accordingly, they are the second elements of novel heel 18 to contact a support surface during ambulation, after the trailing end of central heel extension 46. However, central heel extension 46 is secured at its leading end 48 to the leading end 44 of central support 38 as aforesaid. Thus, when convexity 50 of central support 46 contacts a support surface during ambulation, said convexity is driven upwardly and convexity 17 formed in lateral heel extension 54 and its counterpart formed in medial heel extension 60 are the next parts of heel 18 to contact said support surface. The transition from convexity 50 to convexity 17 and its counterpart occurs very rapidly. The long extent of lateral and medial heel extensions 54, 60 then absorbs the shock of heel impact without causing a vertically upward reaction so that the user does not experience a bouncing sensation as in prior art prosthetic feet.

Moreover, the support of ankle part 14 by horizontal part 40 of central support 38 further ensures against a vertical bounce during ambulation.

This is the first prosthetic foot, anywhere in the world, having a four part heel that includes central support 38, central extension 46, lateral heel extension 54 and medial heel extension 60. It follows that it is the first prosthetic foot to include an ankle part 14 supported by central support 38.

Novel prosthetic foot 10 therefore exhibits a heel elasticity heretofore unknown. It enables a user to jog or run because its unique design absorbs high level impacts in the substantial absence of vertical, bouncing reaction.

Figure 4:
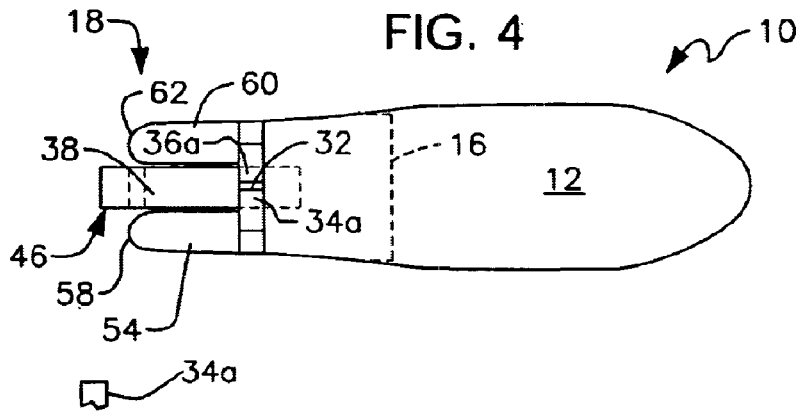
FIG. 4 is a top plan view of a second embodiment of a prosthetic foot with differentiated heel elasticity.
Figure 5:
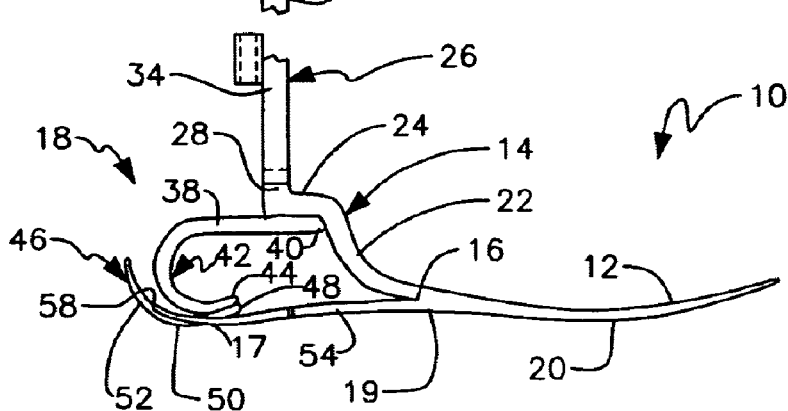
FIG. 5 is a side elevational view of the FIG. 4 embodiment.
Figure 6:
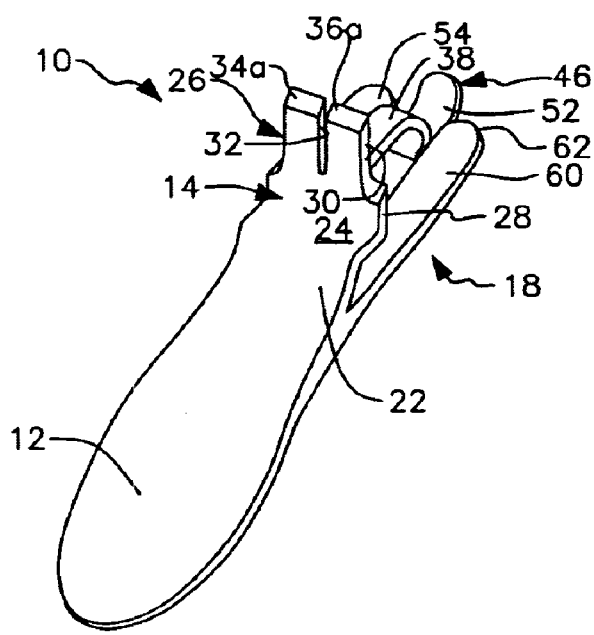
FIG. 6 is a perspective view of the FIG. 4 embodiment.

In the second embodiment of the invention, depicted in FIGS. 4–6, pylon supports 34 and 36 and hence pylon connectors 35, 37 are obviated and supplanted by elongate pylons 34a, 36a that are about twenty inches (20") in length. Said elongate pylons are cut to size by a prosthetist when a patient is fitted with a prosthetic foot. Elongate pylons 34a, 36a eliminate the need for pylon connectors 40, 42 of the first embodiment.

Figure 7:
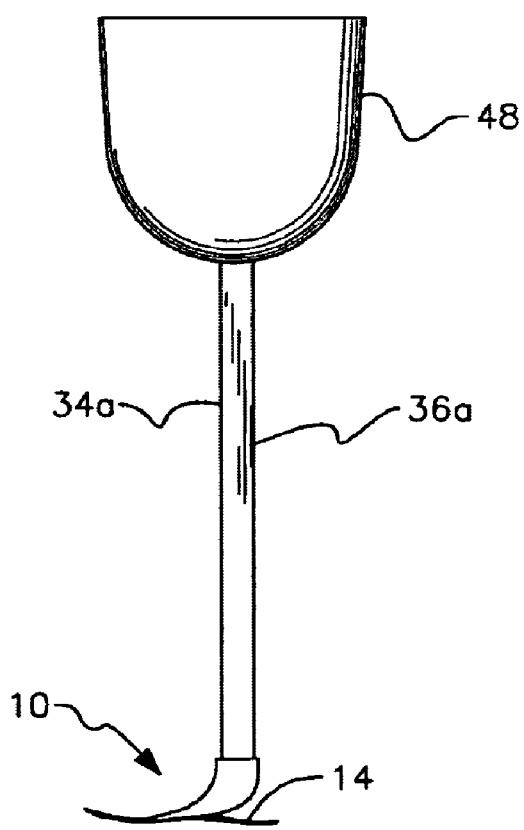
FIG. 7 is a perspective view of the elongate pylons embodiment when attached to a prosthetic socket.

FIG. 7 depicts novel dynamic prosthetic foot 10 when equipped with elongate pylons 34a, 36a.

After pylons 34a, 36a have been cut to a desired length, the prosthetist has several options by which the pylons may be connected to prosthetic socket 48. Pylons 34a, 36a may be laminated into prosthetic socket 48 as illustrated in said FIG. 7. This forms a permanent connection between pylons 34a, 36a and socket 48.

Figure 8:
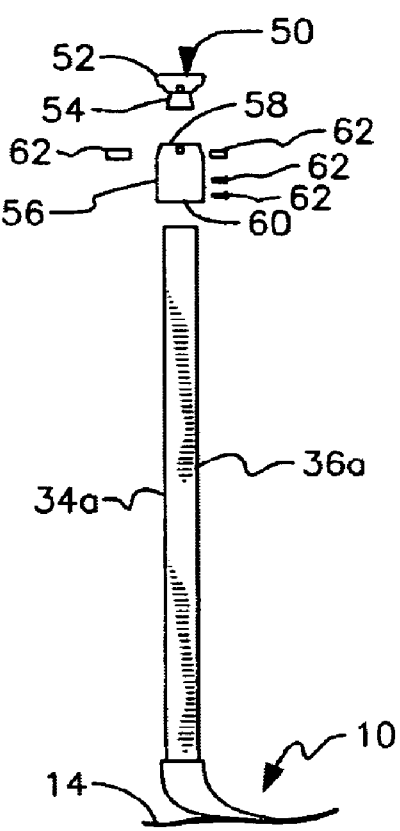
FIG. 8 is a perspective view of the elongate pylons embodiment and further depicting connector means, in exploded form, for connecting said elongate pylons to a socket.

A second option includes the use of a commercially available pyramid connector 50 as depicted in FIG. 8. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 34a, 36a. Lower end 54 of pyramid connector 50 and the respective upper ends of pylons 38a, 39a are captured in said hollow pyramid-receiving connector 56 by a plurality of set screws and other suitable fastening means, collectively denoted 62.

Pyramid connector 52 and pyramid-receiving connector 56 are employed to enable adjustment of the angle of pylons 34a, 36a so that prosthetic foot 10 falls in the correct medial/lateral and anterior/posterior planes, as perhaps best understood by making reference to FIG. 8.

A third option available to the prosthetist after cutting pylons 34a, 36a to their correct length is to laminate the pylons to an unillustrated component and to attach that component to the socket.

Figure 9A:
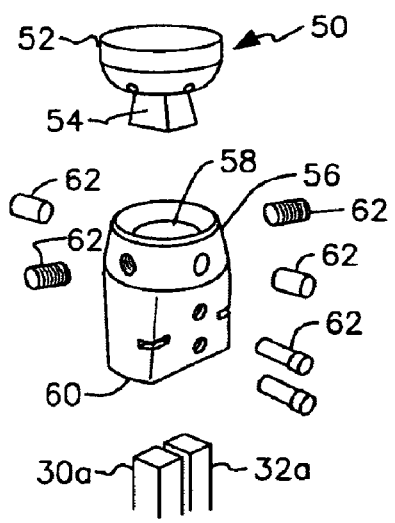
FIG. 9A is an exploded first perspective view of said connector means.
Figure 9B:
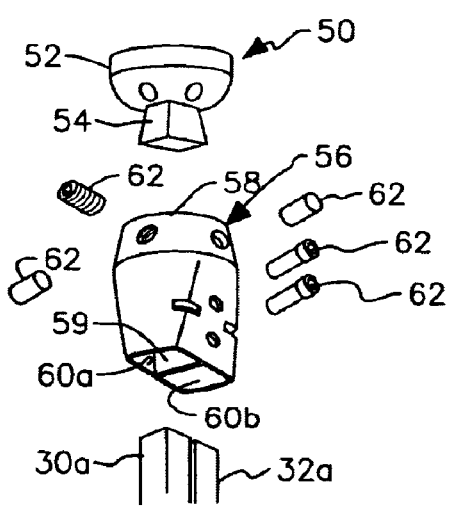
FIG. 9B is an exploded second perspective view of said connector means.
Figure 9C:
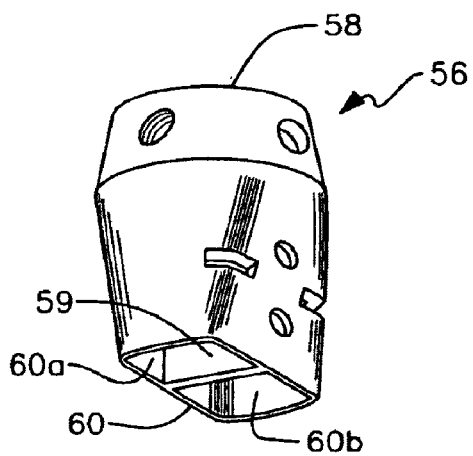
FIG. 9C is a first perspective view of a pyramid-receiving connector.
Figure 9D:
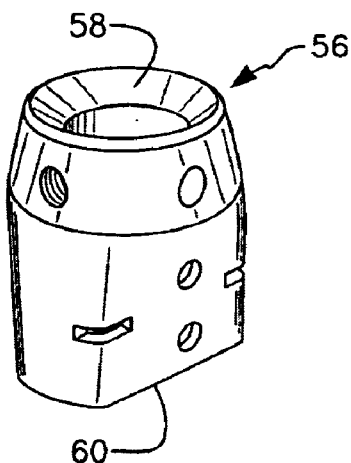
FIG. 9D is a second perspective view of said pyramid-receiving connector.

FIGS. 9A and 9B provide a more detailed perspective view of pyramid connector 50 and pyramid-receiving connector 56. FIGS. 9C and 9D provide a more detailed perspective view of pyramid-receiving connector 56.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
I claim:

1. A dynamic prosthetic foot having a split upper ankle and a heel with differentiated elasticity, comprising:
   a sole;
   an ankle part that separates from said sole along a transverse parting line;
   said ankle part including a gradual upward bend, a horizontal part, and a vertically extending part;
   a vertically extending slot formed in said vertically extending part;
   said vertically extending slot formed mid-breadth of said vertically extending part to divide said vertically extending part into two equal size parts, said two equal size parts forming a lateral pylon support and a medial pylon support, respectively;
   a heel part that separates from said ankle part along said transverse parting line;
   said heel part including a central support, a central extension, a lateral heel extension, and a medical heel extension;
   said central support having a leading end disposed in underlying, supporting relation to said horizontal part of said ankle part and a downwardly turned return bend formed in a trailing end thereof;
   said central extension having a leading end secured to a trailing free end of said central support and a trailing end having a gradual upward bend formed therein;

said lateral heel extension and said medial heel extension being integral and generally coplanar with said sole and being disposed on opposite sides of said central support and said s aid central extension;

whereby said central support, central extension, and medial extension of said heel part provide differentiated responses to impact forces created by ambulation.

2. The dynamic prosthetic foot of claim 1, further comprising:
  a lateral pylon connector secured to said lateral pylon support, said lateral pylon connector adapted for connection to a first prosthetic pylon; and
  a medial pylon connector secured to said medial pylon support, said medial pylon connector adapted for connection to a second prosthetic pylon.

3. The dynamic prosthetic foot of claim 1, wherein said transverse parting line is approximately half way between a leading end of said sole and said trailing end of said central extension.

4. The dynamic prosthetic foot of claim 1, wherein said central extension has a trailing end that trails respective trailing ends of said lateral heel extension and said medial heel extension.

5. The dynamic prosthetic foot of claim 1, wherein said leading end of said central extension is coextensive with the free end of said central support.

6. A dynamic prosthetic foot having a split upper ankle and a heel with differentiated elasticity, comprising:
  a sole;
  an ankle part that separates from said sole along a transverse parting line;
  said ankle part including a gradual upward bend, a horizontal part, and a vertically extending part;
  a vertically extending slot formed in said vertically extending part;
  said vertically extending slot formed mid-breadth of said vertically extending part to divide said vertically extending part into two equal size parts, said two equal size parts forming a lateral pylon and a medial pylon, respectively;
  a heel part that separates from said ankle part along said transverse parting line;
  said heel part including a central support, a central extension, a lateral heel extension, and a medial heel extension;
  said central support having a leading end disposed in underlying, supporting relation to said horizontal part of said ankle part and a downwardly turned return bend formed in a trailing end thereof;
  said central extension having a leading end secured to a trailing free end of said central support and a trailing end having a gradual upward bend formed therein;
  said lateral heel extension and said medial heel extension being integral and generally coplanar with said sole and being disposed on opposite sides of said central support and said central extension;
  whereby said central support, central extension, lateral extension, and medial extension of said heel part provide differentiated responses to impact forces created by ambulation.

7. The dynamic prosthetic foot of claim 6, wherein each of said lateral and medial pylons is about twenty inches (20") in length and is cut to size by a prosthetist when a patient is fitted with said dynamic prosthetic foot.

8. The dynamic prosthetic foot of claim 6, wherein said transverse parting line is approximately half way between a leading end of said sole and said trailing end of said central extension.

9. A The dynamic prosthetic foot of claim 6, wherein said central extension has a trailing end that trails respective trailing ends of said lateral heel extension and said medial heel extension.

10. The dynamic prosthetic foot of claim 6, wherein said leading end of said central extension is coextensive with the free end of said central support.

11. The dynamic prosthetic foot of claim 7, wherein said lateral and medial pylons are adapted to be laminated at respective uppermost ends thereof to a prosthetic socket.

12. The dynamic prosthetic foot of claim 7, wherein said lateral and medial pylons are adapted to be connected at respective uppermost ends thereof to a connector member and wherein said connector member is laminated to a prosthetic socket.

13. The dynamic prosthetic foot of claim 7, wherein said lateral and medial pylons are adapted to be connected at respective uppermost ends thereof to a pyramid-receiving connector that engages a pyramid that depends from a prosthetic socket.

* * * * *